United States Patent
Habibi-Naini et al.

(10) Patent No.: US 8,646,662 B2
(45) Date of Patent: Feb. 11, 2014

(54) DEVICE FOR DISPENSING A FILLING MASS

(75) Inventors: Sasan Habibi-Naini, Rikon (CH);
Florian Hüsler, Zug (CH)

(73) Assignee: Sulzer Mixpac AG, Haag (CH)

( * ) Notice: Subject to any disclaimer, the term of this patent is extended or adjusted under 35 U.S.C. 154(b) by 105 days.

(21) Appl. No.: 13/138,214

(22) PCT Filed: Mar. 5, 2010

(86) PCT No.: PCT/EP2010/052827
§ 371 (c)(1),
(2), (4) Date: Jul. 20, 2011

(87) PCT Pub. No.: WO2010/102955
PCT Pub. Date: Sep. 16, 2010

(65) Prior Publication Data
US 2011/0273956 A1    Nov. 10, 2011

(30) Foreign Application Priority Data
Mar. 11, 2009  (EP) ..................................... 09154942

(51) Int. Cl.
*B65D 83/00*  (2006.01)
*B01F 5/06*  (2006.01)
(52) U.S. Cl.
USPC .......................................... 222/459; 366/336
(58) Field of Classification Search
USPC ................................................ 366/336–340
See application file for complete search history.

(56) References Cited

U.S. PATENT DOCUMENTS

| 1,473,165 | A | * | 11/1923 | Steigmeyer ..................... 118/63 |
| 4,995,540 | A | * | 2/1991 | Colin et al. ................... 222/132 |
| 5,397,180 | A | | 3/1995 | Miller |
| 5,413,253 | A | | 5/1995 | Simmen |
| 5,722,829 | A | | 3/1998 | Wilcox |
| 5,916,491 | A | * | 6/1999 | Hills .............................. 261/91 |
| 2003/0185098 | A1 | * | 10/2003 | Koch et al. .................... 366/336 |
| 2007/0017938 | A1 | * | 1/2007 | Thompson et al. ........... 222/527 |

FOREIGN PATENT DOCUMENTS

| EP | 1 8125 927 A | 8/2007 |
| FR | 2 661 097 A | 10/1991 |
| WO | WO 01/74253 A | 10/2001 |
| WO | WO 2004/105856 A | 12/2004 |

* cited by examiner

*Primary Examiner* — Tony G Soohoo
*Assistant Examiner* — Anshu Bhatia
(74) *Attorney, Agent, or Firm* — Francis C. Hand; Carella, Byrne et al.

(57) ABSTRACT

An apparatus for the injection of a fluid filler material includes a static mixer (1), with the static mixer including a housing (2) which includes a first hollow space (47), with at least one mixer element (3) being arranged in the first hollow space. The housing (2) has an outlet element (45). The outlet element (45) has a second hollow space (48), with the second hollow space (48) being connected to the first hollow space (47) such that the fluid filler material can be conducted from the first hollow space (47) into the second hollow space (48). A tubular element (60) is held in the second hollow space (48).

20 Claims, 8 Drawing Sheets

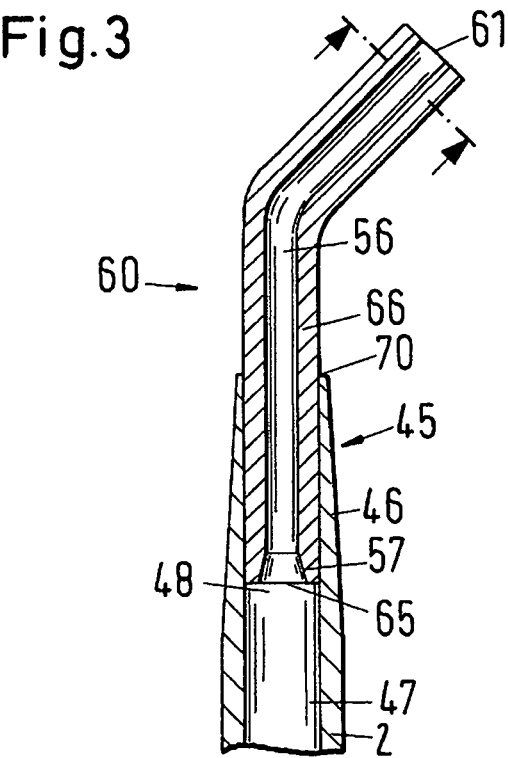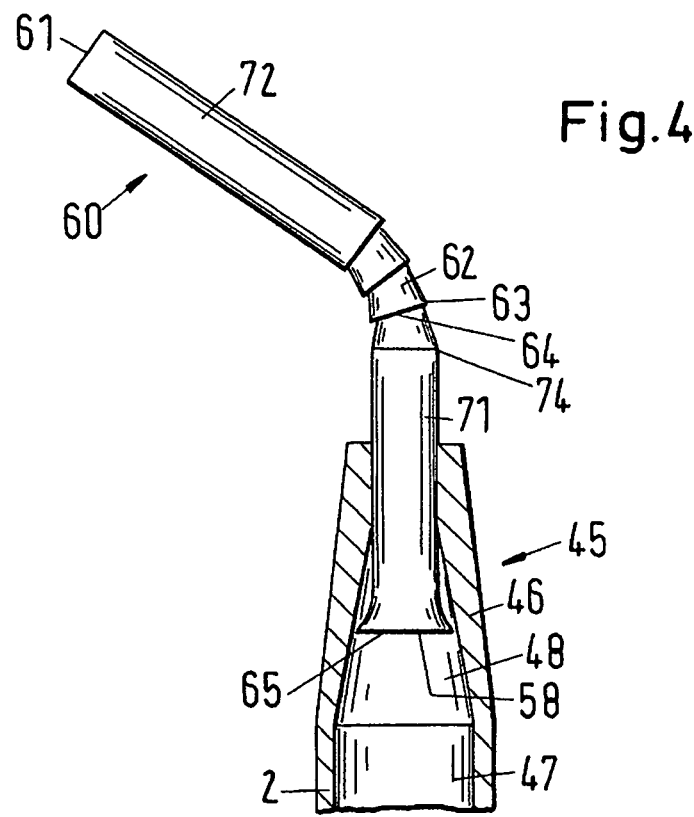

Figure 1:
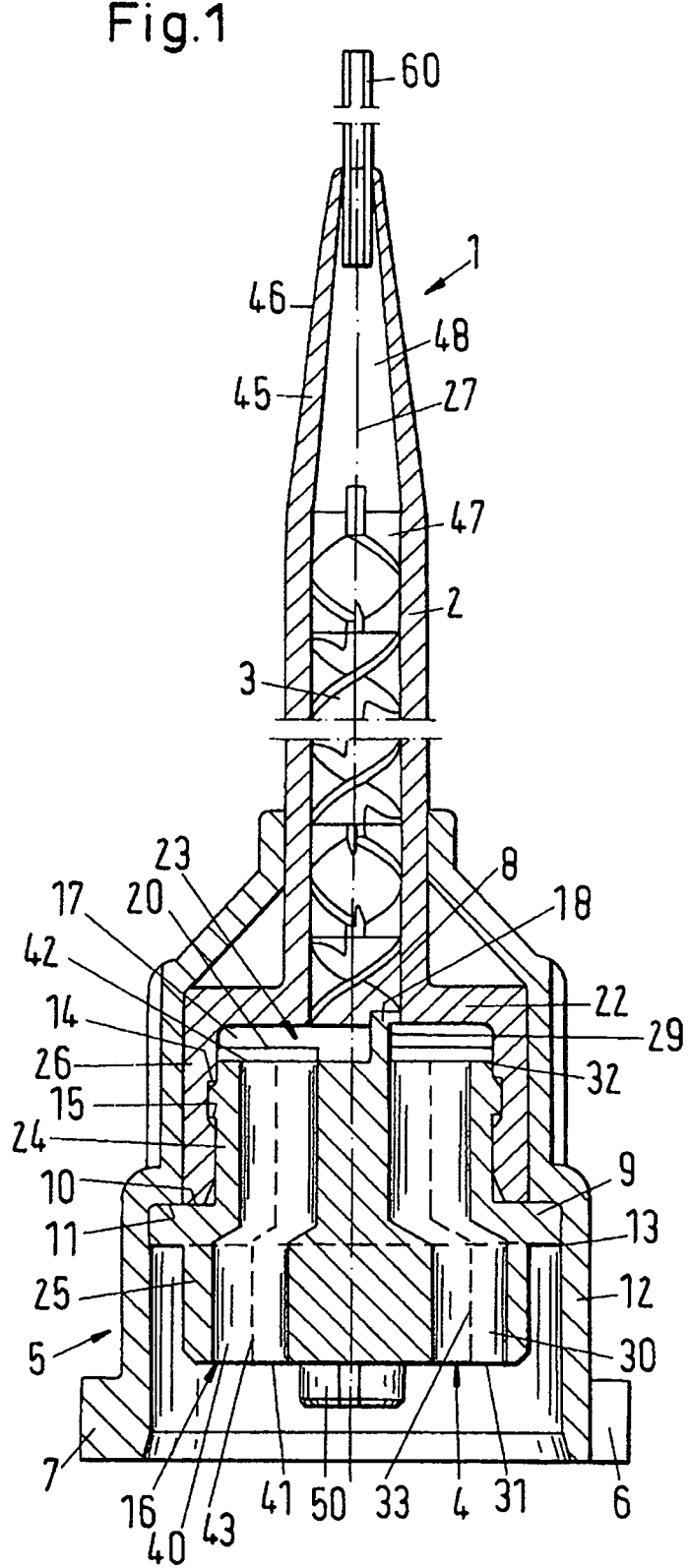

Fig.10
Fig.11
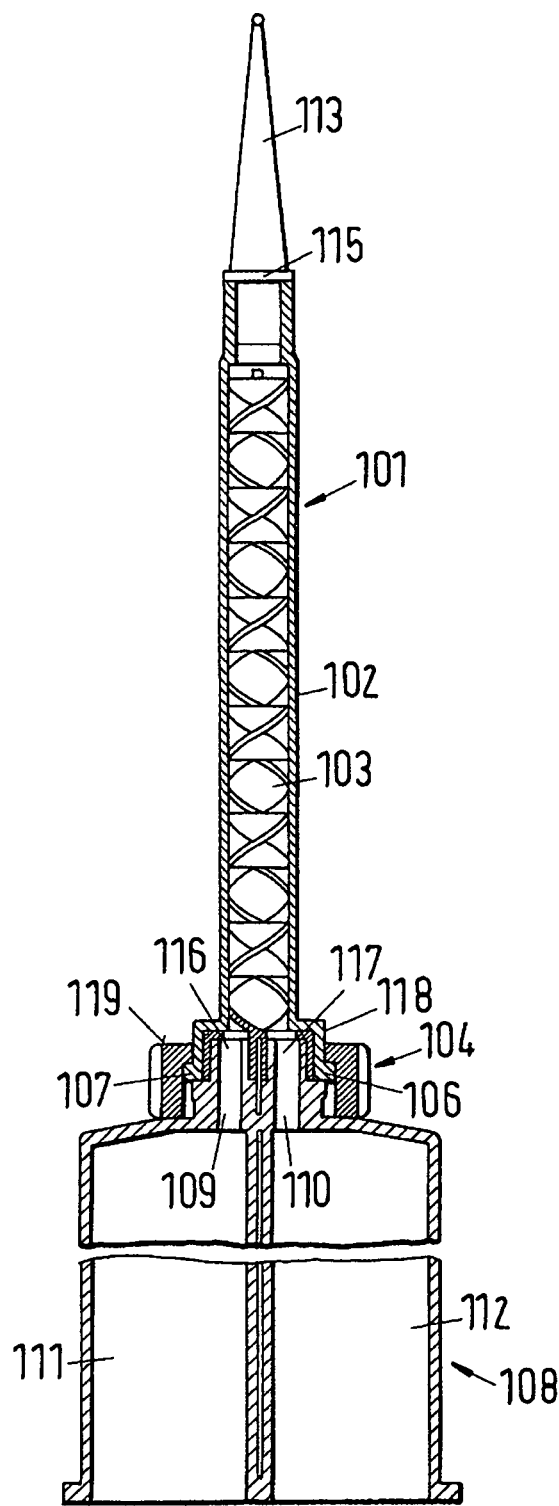
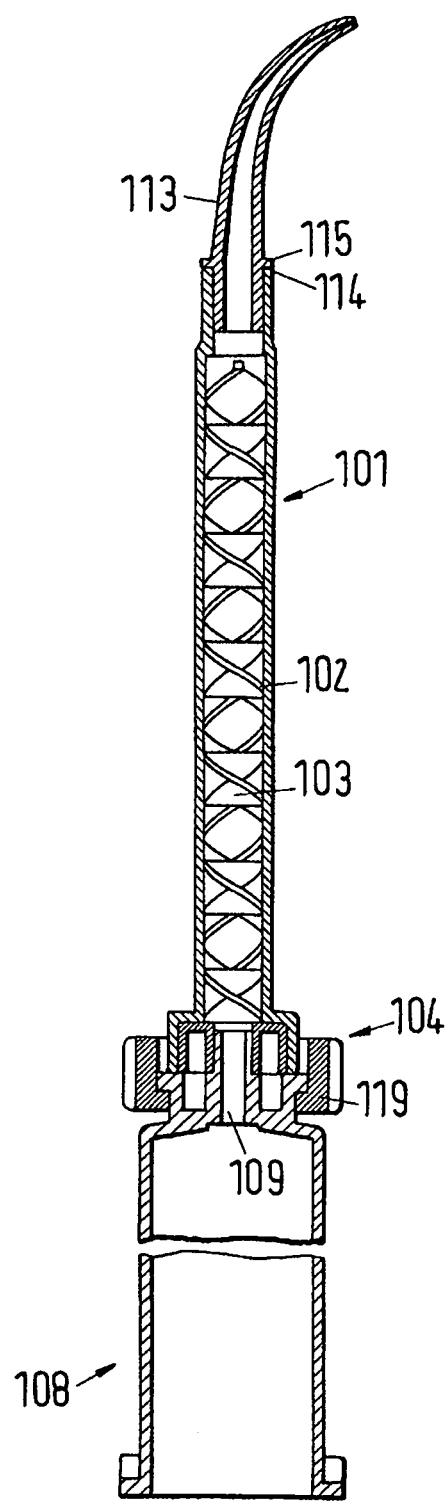

DEVICE FOR DISPENSING A FILLING MASS

The invention relates to an apparatus for the discharge of a fluid filler material. The apparatus is attachable to a static mixer to bring the filler material which has been mixed in the static mixer precisely to the destination location.

A dispensing arrangement made up of a multicomponent dispensing device and a multicomponent cartridge as well as a static mixer is known, for example, from EP 0 730 913. A multicomponent cartridge includes at least one storage container for components to be mixed and is in particular made as a dispensing cartridge which can be emptied by means of a dispensing device. Such a dispensing device can include means for the reduction of the filling volume of the storage container. A dispensing device can in particular be made as a dispensing gun. In accordance with this already known solution, the static mixer also includes a connection piece which is designed for assembly with the cartridge. The static mixer and the connection piece are in this respect made as a single component which can be manufactured in the injection molding process.

It is furthermore known to use attachments which are placed onto the discharge end of the static mixer. They have the function of applying the filler material more precisely at the place of use, for example at an adhesion point. Such attachments are also known to introduce filler materials directly into hollow spaces. These attachments are used, for example, to fill cavities in teeth which have arisen due to a dental treatment. Such an attachment available on the market is shown, for example, in FIG. 10 or FIG. 11.

It is known from WO2004/105856 to foresee a tubular element, by which the filler material can be introduced into narrow deep cavities. The tubular element is held in a transition piece which has an insertion end, which is pushed into the mixer outlet an a conical retention element provided with slits. The slits define retention lamellae. In order to hold the tubular element safely in the retention lamellae, a fixing element is pushed over the transition piece. Hereby the width of the slit is decreases as the retention lamellae of the transition piece are squeezed. Thereby the tubular element is safely retained in the transition piece.

It is thus the object of the invention simplify the assembly of the apparatus, in particular of the tubular element. The tubular element is arranged downstream of the static mixer. A further object of the invention is to decrease the number of required parts for the assembly of the apparatus. A further object of the invention is therefore to simplify the assembly by deceasing the number of steps required for the assembly of the apparatus.

It is a further object of the invention to provide an orientable apparatus by means of which it is possible to introduce filler material into cavities difficult to access.

This object is satisfied by means of an apparatus for the injection of a fluid filler material. The apparatus includes a static mixer, with the static mixer having a housing which includes a first hollow space, with at least one mixing element being arranged in the first hollow space. The housing has an outlet element, with the outlet element having a second hollow space, with the second hollow space being connected to the first hollow space such that the fluid filler material can be conducted from the first hollow space into the second hollow space. A tubular element is held in the second hollow space, whereby the housing is configured as a fastening element for the tubular element.

The tubular element can have an outer diameter of a maximum of 3 mm, preferably of a maximum of 2.5 mm, particularly preferably of 1.5 mm.

A maximum inner diameter of approximately 2.5 mm hereby results for a maximum outer diameter of 3 mm; a maximum inner diameter of approximately 2 mm for a maximum outer diameter of 2.5 mm and a maximum inner diameter of approximately 1 mm for a maximum outer diameter of 1.5 mm.

Since the filler material has to overcome a pressure loss increasing with the length of the tubular element, the tubular element has a length of a maximum of 100 mm, preferably of a maximum of 50 mm, particularly preferably of a maximum of 30 mm.

The outlet element includes a cone in accordance with a preferred embodiment. Such a cone is provided to reduce the material consumption of the outlet element and to optimize the outlet element for injection molding technology. The wall thickness thus decreases in the direction of the opening of the outlet element. A decreasing wall thickness is advantageous from a technical injection molding aspect since the melt which reaches the outlet element at the latest moment requires a shorter cooling time as less melt has to be cooled due to the decreasing wall thickness. The total cooling time for the melt can thus be reduced by the design of the outlet element as a cone.

The second hollow space can also be made conical so that the tubular element can be mounted easily and can be held in the hollow space. The tubular element can in particular have an extension, which can be fit into such a cone, at the end which is aligned in the direction of the static mixer. If the smallest inner diameter of the cone is smaller than the outer diameter of the tubular element at the end through which the filler material can be discharged, the tubular element is held in the cone by a press fit. The hollow space can also have a plurality of sectionally conical sections in which the tubular element is held at a plurality of contact points.

The angle of inclination of the cone of the outlet element and of the conical second hollow space can differ. The angle of inclination of the outlet element can in particular be larger than the angle of inclination of the conical second hollow space.

A conically formed second hollow space is also advantageous for the flow of the filler material. The filler material coming from the discharge end of the mixer has to be conveyed, into the inlet cross-section of the tubular element. If the cross-section of the second hollow space is only reduced gradually and continuously, the pressure loss of this flow can be kept low. This in turn has the consequence that the required contact pressure which the dispensing device exerts onto the cartridge can be lower. The pressure loss is also additionally reduced by use of an intermediate piece in accordance with FIG. 1 or FIG. 2 so that a particularly low pressure loss results by a combination of the intermediate piece and an outlet element which has a second conical hollow space.

The second hollow space can also have an inner diameter at least over a part of its length which is smaller than the outer diameter of the tubular element. In this case a press fit also results. It is a further advantage of the use of a press fit that it is leak tight against the passage of filler material. The filler material is therefore only discharged through the opening aperture of the tubular element, but not through a gap between the tubular element and the outlet element so that the total filler material has to pass the tubular element to be applied at the desired location of application.

The tubular element is advantageously bendable so that the position of the opening aperture of the tubular element can be changed relative to the mixer. The property that the tubular element is bendable can, be due to the fact that the material of the tubular material itself is bendable. Alternatively or in addition thereto, the tubular element can include at least one bending element. For example, a bending element can include a plurality of thickened portions. Regions with a lower wall thickness are arranged between adjacent thickened portions and can be deformed more easily than the two regions of the tubular element which extend from the thickened portions and which have a larger wall thickness than the wall thickness between adjacent thickened portions. The thickened portions can be made as ribs or scales, for example. A thickened portion is defined in this respect as a section in which the wall thickness is larger than in the two directly adjoining sections. The wall thickness can be larger or also the same as the wall thickness of the tubular element in this respect; it is important that the wall thickness is smaller locally between adjacent thickened portions than the wall thickness of the tubular element in the direction of the inlet opening or of the opening aperture.

In accordance with a further variant, the bending element is made such that the bending element has a tubular bellows structure or corrugated structure. The bellows structure includes at least one ring fold of a zigzag shape which forms the bellows structure in this embodiment when seen in an axial section. This or each fold is made up of a first side and of a second side and of an edge which is enclosed by the two sides. The edge will from now on be called an uphill edge. As a rule, a plurality of these folds are arranged in rows next to one another and form the bellows structure in this manner. Adjacent folds are connected via an edge which connects the right hand side end of the first fold arranged on the left hand side to the left hand side end of the second fold arranged on the right hand side. This edge will be called a downhill edge in the following. A first uphill edge thus follows a first downhill edge in the region of the bending element and a second downhill edge then adjoins the first downhill edge. The first fold extends between the first downhill edge and the second downhill edge. A second fold, which is bounded by the second downhill edge and by a third downhill edge, follows the first fold. The second uphill edge of the second fold rises between the second downhill edge and the third downhill edge. The jacket of the tubular element is kinked along each of the edges. The wall thickness of the edges in this respect substantially corresponds to the wall thickness of the sides. If the bending element is already produced during the manufacture of the tubular element, the wall thickness of the bellows structure can be set as desired. The wall thickness can in particular be selected such that, in the folded state, the tubular element extends along a straight longitudinal axis and remains stable in the straight position. This type of manufacture is in particular suitable for tubular elements which are manufactured in the injection molding process in a single workstep.

The bellows structure can alternatively to this also be applied subsequently after completion of the bending element by plastic deformation of the tubular element. In this case, the tubular element is manufactured by extrusion or by a corresponding continuous manufacturing process for a semifinished part from a metallic material which is subsequently cut to the desired length and the bellows structure can be applied subsequently by means of a shaping process which can include a stamping process or a pressing process. Alternatively, for tubular elements made of plastic the bellows structure can be applied directly subsequently to the extrusion of the tubular element 60.

The bellows structure has the effect that the tubular element has a straight longitudinal axis as long as no forces are applied to the tubular element by means of which a curvature can be generated. However, if bending forces are applied to the bending element which are aligned normally to the longitudinal axis or at least have force components in a direction normal to the longitudinal axis, the straight longitudinal axis is curved in the region of the bending element. The bending element can be plastically deformed in the edges of the folds by the effect of the bending forces so that the bend of the bending element is irreversible and the bending element remains in the curved position. A stability against kinking is additionally ensured by the peripheral bellows structure. This means that the inner cross-sectional surface of the tubular element in the region of the bending element does not deviate substantially from the inner cross-sectional surface of the first and second sections which adjoin the bending element.

In addition to the preceding statements relating to a bending element which includes a bellows structure, a provision can also be made for maintaining the bellows structure under a pre-stress condition. In particular if the angle included between two adjacent sides becomes small, that is tends toward zero, a pretension can be applied during the manufacture of the tubular element which holds the folds in a tightly contacting position with respect to one another. This means that the spacings between adjacent folds are so small that the folds are supported on one another.

If a curvature should be applied to the bending element and if this curvature of the bending element should be maintained as long as the dispensing of the filler material takes place, the pretension is overcome by application of a tensile force onto the bending element. The angle included between adjacent sides is enlarged when a tensile force is applied onto the bending element. The adjacent sides can now no longer support one another and can no longer impede a curvature. A force is then applied to set the desired curvature. The material can be locally plastically deformed at least in one part of the edges by this force so that the curvature of the bending element is maintained once it is applied. The curvature should in particular not change at least for the duration of the dispensing of the filler material, that is the curvature radius and the angle the two first and second sections of the tubular element extending from the bending element include with one another.

The tubular element furthermore has a widened portion of the passage in the region of the inlet opening. This widened portion serves for the fixing of the tubular element in the outlet element. The tubular element is held fixedly in the hollow space and can in particular not be pushed out of the second hollow space by the pressure of the filler material. The inner diameter of the second hollow space can be smaller than the outer diameter of the tubular element, at least in the region adjacent to the discharge opening, so that a press fit results.

On assembly, the tubular element is pushed into the second hollow space from the mixer side. The tubular element is then driven through the second hollow space, for example, by one blow or by a series of blows by means of an assembly tool while applying a compressive force until a large part of the tubular element projects out of the discharge opening. The widened portion can in this respect serve for centering of the assembly tool and for the transmission of the impact force.

Alternatively to this, the tubular element, can also be placed into the tool for the outlet element or the mixer housing in accordance with one of the preceding embodiments. The tubular element is overmolded in this case, which signifies that is surrounded by a plastic melt during the injection molding process said plastic melt being subsequently cooled. In accordance with this variant, the tubular element is thus inserted in a single workstep contemporaneously with the manufacture of the mixer housing. It can also be ensured by this method that the cross-sectional surface of the tubular element at the inlet opening is the same as the cross-sectional surface of the second hollow space at this point.

In accordance with a further variant the tubular element is placed into the tool for the mixer housing without widening. The inlet opening of the tubular element is engaged by a tool mandrel which is movable. If the tool or the tool mandrel are moved such that the shape of the mixer housing to be manufactured is obtained, the tool mandrel is introduced into the inlet opening of the tubular element. The inlet opening of the tubular element is stretched during this movement of the tool mandrel or of the tool, whereby the material of the tubular element is subjected to a plastic deformation. This variant has the advantage that a preceding or subsequent workstep of the widening can be omitted since the widening can already take place during the manufacture of the mixer housing and of the outlet element.

Alternatively to this, it is possible to fasten and hold the tubular element in accordance with one of the preceding embodiments in the second hollow space by means of a snap connection or by means of a holding connection or by means of an adhesive bond.

The tubular element in accordance with one of the preceding embodiments can furthermore be arranged to be rotatable relative to the static mixer.

In accordance with a further preferred embodiment, the tubular element includes a jacket of metal. A tubular element of metal is simple to manufacture and can be bent manually into any desired position. The user can thus adapt the position of the opening aperture of the tubular element in a simple manner to the desired application location of the filler material. A bending element in accordance with one of the preceding embodiments can also be provided.

The advantage of the use of a bendable tubular element or of a bending element in accordance with one of the preceding embodiments can be found in the fact that a position of the tubular element is maintained once it has been selected. The type of deformation is a deformation in the plastic region and not a deformation in the elastic region, because in the latter case a restoration into the original shape would occur after removal of the force applied having caused the deformation.

The jacket of metal can be covered with a plastic layer. The use of a plastic layer is in particular advantageous in applications in which the filler material has to be applied in a corrosive environment. The use of plastic is also advantageous in the dental area if the filler material is, for example, a tooth filling or an impression compound for the manufacture of a dental crown. Plastic is felt to be a more pleasant material by patients since it feels warmer and is softer than a metallic surface.

Alternatively to this, the tubular element can include a jacket of plastic. The tubular element can thus be made from a plastic which is preferably bendable or contains a bending element in accordance with one of the preceding variants.

To stabilize the tubular element, the tubular element can also include a core element which is arranged inside the tubular element. The core element can be made as a metal pin, for example, or can be made in wire form. The core element can in particular be used for the setting of the position of the opening aperture of the tubular element. The jacket of the tubular element can be made from any desired deformable material. The deformation of the material of the jacket can in this case be in the elastic region or in the plastic region. The tubular element must be suitable to conduct the filler material being discharged from the static mixer to the desired location of use. However, the fixing of the position of the opening aperture is, taken over by the core element. The core element can extend freely in the interior of the tubular element or it can be connected to the tubular element by means of a connection element. A plurality of connection elements can also be arranged at different locations in the tubular element.

Alternatively to this, the core element can be at least partly enclosed by the jacket of the tubular element. It is avoided in this case that the core element can induce an additional flow resistance in the tubular element. The flow path is kept very largely free for the passage of the filler material.

The core element can be made in wire form. The core element can in particular contain a metal.

Alternatively, the core element can also be completely received in the wall of the jacket of the tubular element. A plurality of core elements can also be provided which form a reinforcing structure. The core elements can also be made as a fiber, felt, fabric or knitwear which is surrounded or enclosed at least partly by the material of the jacket of the tubular element.

The static mixer can in particular be used for the mixing of a hardening mixed product of flowable components.

A further possible use of the static mixer is the mixture of impression compounds in the dental field or the mixture of multicomponent adhesives or the mixing of hardening filler compounds in the construction sector, for example chemical dowels or anchorage elements.

Figure 2:
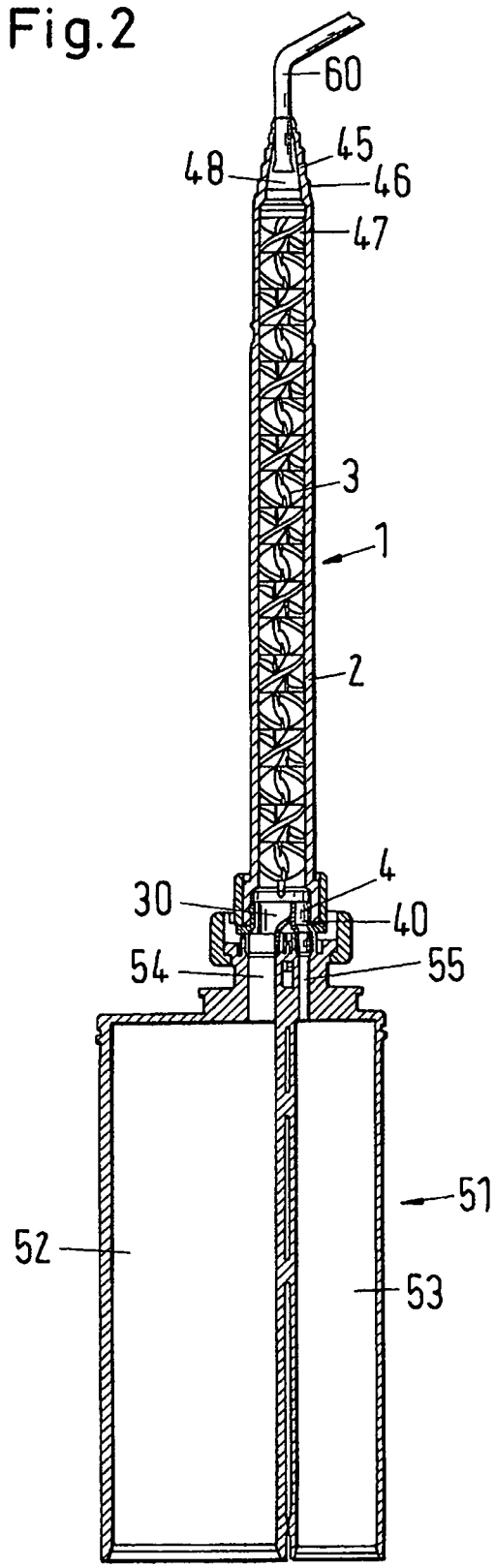
Figure 5:
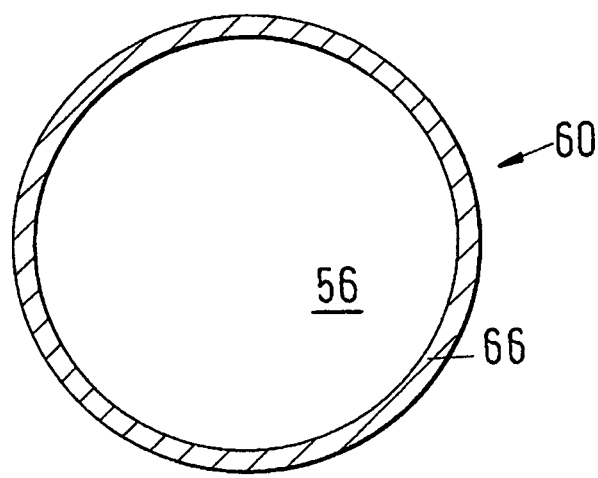
Figure 6:
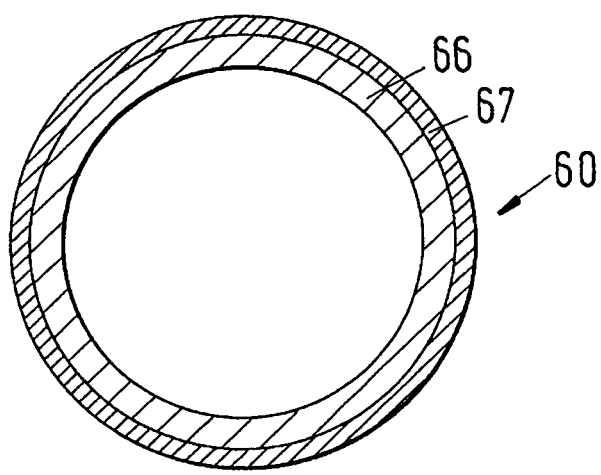
Figure 7:
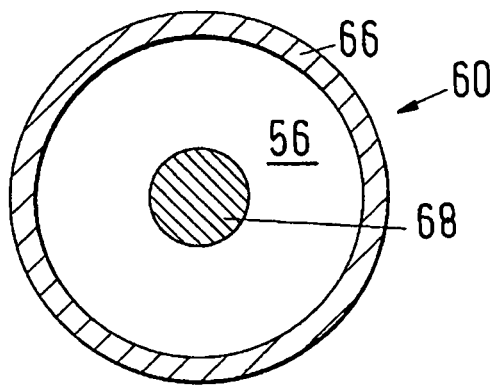
Figure 8:
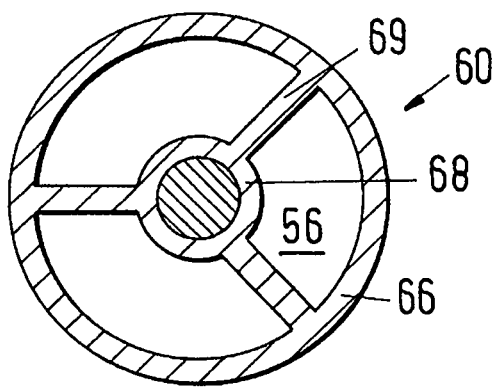
Figure 9:
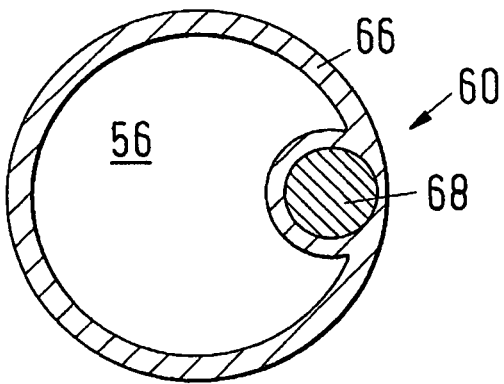
Figure 12:
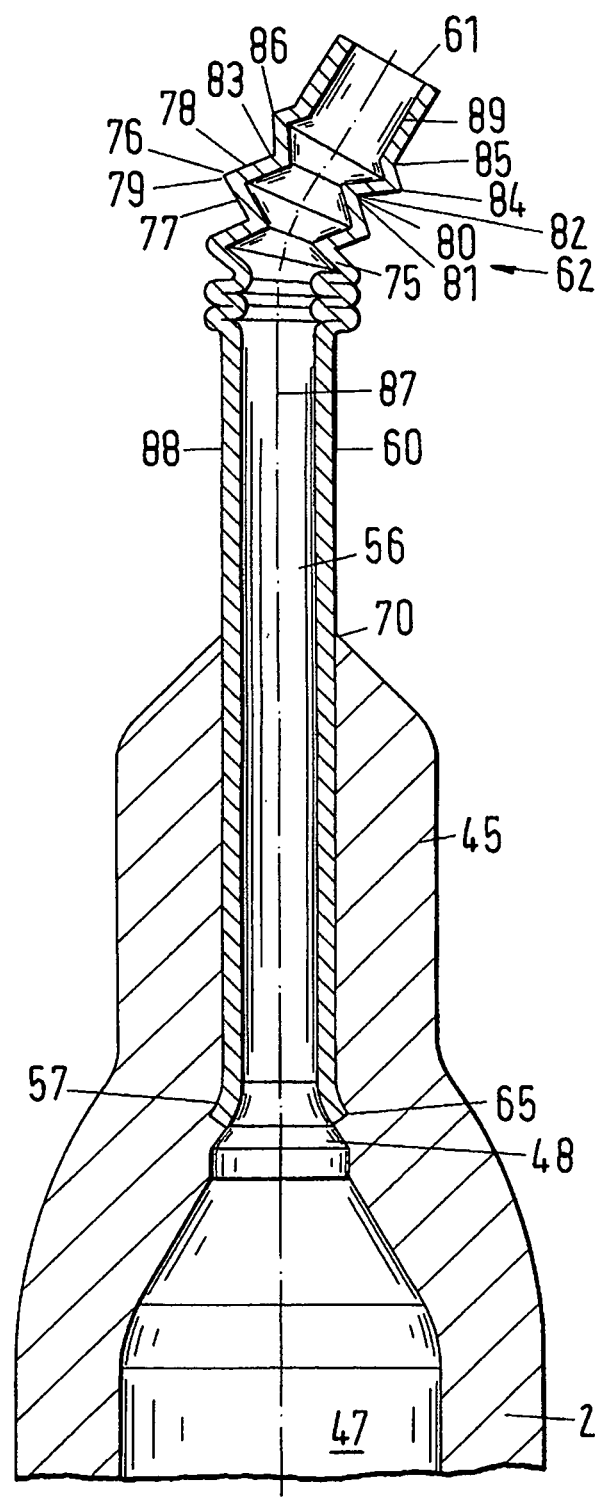
Figure 13:
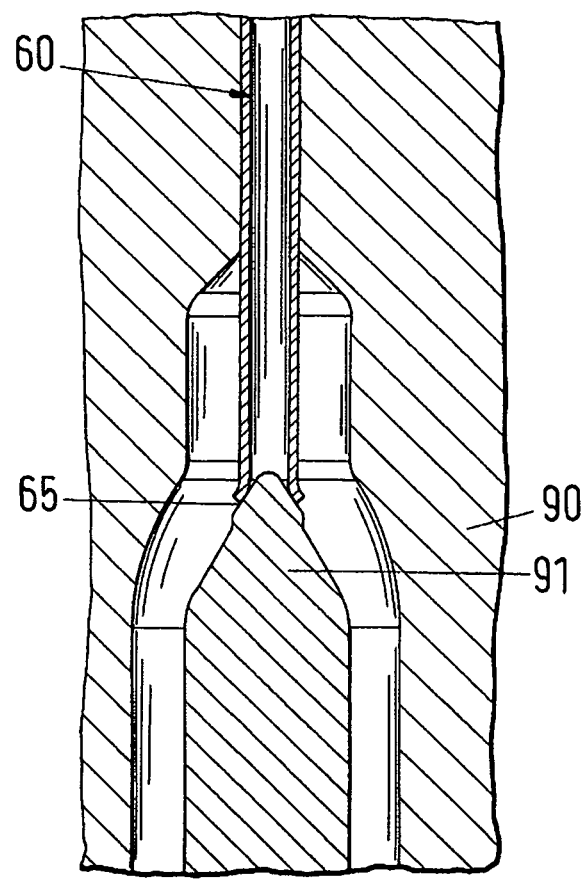

The invention will be explained in the following with reference to the drawings. There are shown:

FIG. 1 a section through an apparatus for the injection of a fluid filler material in accordance with a first embodiment of the invention;

FIG. 2 a section through an apparatus for the injection of a fluid filler material in accordance with a second embodiment of the invention;

FIG. 3 a section through a tubular element in accordance with a first embodiment of the invention;

FIG. 4 a view of a tubular element in accordance with a second embodiment of the invention;

FIG. 5 a section through the tubular element of FIG. 3 along the plane A-A;

FIG. 6 a section of a third embodiment of the tubular element in accordance with the invention;

FIG. 7 a section of a fourth embodiment of the tubular element in accordance with the invention;

FIG. 8 a section of a fifth embodiment of the tubular element in accordance with the invention;

FIG. 9 a section of a sixth embodiment of the tubular element in accordance with the invention;

FIG. 10 an attachment from the prior art;

FIG. 11 a section through the attachment of FIG. 10;

FIG. 12 a view of a tubular element in accordance with a seventh embodiment of the invention;

FIG. 13 a further variant for the manufacture of a tubular element.

FIG. 1 shows a section through a static mixer 1 with an intermediate piece 4 and a tubular element in accordance with a first embodiment of the invention. This static mixer 1 for a cartridge for the reception of one component or in particular of a plurality of components includes a mixer housing 2 which contains at least one static mixing element 3, can in particular be made up of a plurality of mixing elements, so that a number of similar mixing elements preferably forms a group of mixing elements. Such mixing elements are, for example, known from EP 749776 B or EP 1426099 B1 or have a helical structure as shown for the helical mixer. The mixer has the function of stirring the individual components well so that a substantially homogeneous mixture results. The mixer could also be made as a dynamic mixer (not shown). A dynamic mixer differs from the static mixer in that the mixing elements are arranged to be movable relative to the mixer housing.

The mixer shown in FIG. 1 can be used for the homogenization of a component or for the mixing of two or more components in the same manner. The components can be in a mixing ratio to one another which differs from a 1:1 mixing ratio. The static mixer in accordance with FIG. 1 is fastened to the cartridge by means of a ring-shaped coupling element 5. The coupling element 5 contains the inlet region of the housing 2 of the static mixer as well as the intermediate piece 4 which contains a first passage 30 and a second passage 40 which guide a respective component to the static mixer. More than two passages can naturally also be contained in the intermediate piece 4 if more than two components should be supplied to the static mixer 1 separately from one another. The coupling element 5 can be fastened to the cartridge by means of a bayonet fastening means 6, 7, for example. In accordance with an embodiment, not shown in the figures, the coupling element could also have a connection element which engages into a mating element of the cartridge to form a latch connection, for example. The static mixer 1 can thus be fastened to the dispensing cartridge or to the dispensing device by means of the coupling element 5 together with the intermediate piece 4.

Alternatively to this, the coupling element 5 can have an external thread by means of which it can be screwed to the cartridge.

The inlet region of the housing 2 of the static mixer has an inlet end 10 which serves for the reception of the intermediate piece 4. The intermediate piece includes a first connection element 24 and a second connection element 25 which are separated from one another by a holding flange 9. The first connection element 24 is received in the interior of the inlet region and can be held in the inlet end 10 by a retention flange 14 which engages into a peripheral groove 15 of the inlet end 10. The first connection element 24 is thus designed for the reception of a housing of a static mixer. The flange 9 adjoining the first connection element 24 serves as a support for the inlet end 10 of the housing of the static mixer. The first connection element 24 as well as the second connection element 25 are cylindrical in this embodiment, but could also have a quadrangular, diamond-shaped, rectangular, round, oval or another cross-sectional surface matching the associated inlet end 10 with the same manner of operation. The first connection element 24 can have a positioning element 29 for the alignment of the static mixer with respect to the connection element. A plurality of positioning elements, in particular two, can also be provided. This measure is advantageously used in mixers in which the mixing quality changes dependent on the position of the mixing elements with respect to the position of the intermediate piece. The positioning element 29 in particular indicates the ideal position of the static mixer 1 with respect to the intermediate piece 4. For this purpose, the positioning element 29 can be made as a projection which also visibly shows the position of the static mixer 1 with respect to the intermediate piece 4 and thus also provides an aid for the assembly. The first connection element 24 includes a jacket surface to which the projection is attached. The second connection element 25 adjoins the oppositely disposed side of the flange 9 and is designed for assembly with the cartridge.

In accordance with a further variant, not shown in the drawing here, the first or the second outlet opening 32, 42 can be made such that it can be aligned in a matching position to the static mixer. The shape of the cross-sectional surface of at least one of the first or second inlet openings 32, 42 is in particular preferably not rotationally symmetrical, in particular oval or rectangular or diamond shaped.

The first connection element 24, the flange 9 and the second connection element 25 contain the first and second passages 30, 40. The second connection element 25 can include an encoding means. The intermediate piece 4 is in particular designed such that the first passage 30 has a first center axis 33 and the second passage 40 has a second center axis 43. The second connection element 25 includes a first encoding means 50 and, optionally, a second encoding means. The first encoding means 50 can in particular be arranged oppositely disposed the second encoding means with respect to a plane which is spanned by the first and second center axes 33, 43 of the passages 30, 40.

The first encoding means 50 is in particular made as an arm, whereby the arm also could also be called a web. The arm has a finger element which is designed for the engagement into an associated cut-out of the dispensing unit or of the dispensing cartridge. The finger element can be made as an axial rail which is designed for the engagement into an associated groove of the cartridge.

The encoding means 50 can also be designed as a groove in the outer jacket of the second connection element 25, which is not shown in the drawing here.

If two or more encoding means 50 are provided, the encoding means also do not have to be arranged disposed opposite to one another. If two or more encoding means are provided, the cross-sectional surface of at least one of the encoding means should differ from the cross-sectional surface of the further single or plurality of encoding means, in particular if the encoding means are arranged symmetrically to one another.

Alternatively to this, a plurality of encoding means 50 can also have an asymmetrical arrangement on the inlet side. Due to the asymmetric arrangement which is reflected in the same away on the dispensing cartridge or on the dispensing device, an unambiguous positioning of the intermediate piece and thus of the static mixer connectable to the intermediate piece with respect to the dispensing cartridge or to the dispensing device can take place.

The cross-sectional surface of the first inlet opening 31 can differ from the cross-sectional surface of the second inlet opening 41. The element 16 has the function of an optical encoding means in this embodiment. An element 16 made for example as an oval, polygonal, in particular quadrangular or diamond-shaped cross-sectional surface is visually clearly recognizable so that the static mixer 1 can be aligned in an unambiguous position with respect to the element 16 on the assembly. The shape of the cross-sectional surface of at least one of the first or second inlet openings 31, 41 is preferably not rotationally symmetrical, in particular oval or polygonal, in particular rectangular or diamond-shaped.

The intermediate piece 4 is held in the housing 2 of the mixer via the retaining flange 14. The flange 9 is matched to the inlet end 10 of the housing 2 and contacts a shoulder 11 of the inner wall of the coupling element 5. The intermediate piece 4 has an end face 20 at its outlet-side end plate. This end face 20 can be equipped with a guide element, which is in particular made as a dividing edge 17 and/or as a partial barrier 18, for the deflection of the component flows so that the components have to flow substantially perpendicular to the longitudinal axis 27 of the mixer and parallel to the end face 20 toward a divider edge 8. The divider edge 8 is the edge of the first static mixing element 3 which faces the intermediate piece 4 and comes into contact with the two components.

The end face 20 contains the two outlet openings 31, 41 of the passages 30, 40. The dividing edge 17 is attached to the end face 20 such that each component which is discharged through the two outlet openings 31, 41 is already divided by the dividing edge 17 into two part flows, in particular into two halves. The part flows of each of the components combine in a collection chamber 23. Subsequently, the flows in the collection chamber are divided again by the divider edge 8 of the static mixer. The dividing edge 17 and the divider edge 8 advantageously stand normally on one another. This has the advantage that the component flow is divided into two part flows which differ in their composition from the part flows generated by the dividing edge 17. A first mixing stage hereby already hereby results even before the entry of the components into the static mixing elements 3 of the static mixer 1. In particular when the mixing ratio of the components differs from a 1:1 mixing ratio, the division of each component into at least two part flows and the subsequent combination of each of the part flows correspond to a first mixing stage because it is then ensured that the component which has the smaller volume portion enters in equal parts into the first mixing element 3 of the static mixer. Each of the part flows thus contains a portion of the first and of the second components corresponding to the mixing ratio. The entry conditions into the static mixer are thus improved by this first mixing stage. In addition to the dividing edge 17, a partial barrier 18 and further installations for the redirection of the flow in the direction of the two part spaces of the mixing space of the static mixer divided by the divider edge 8 can be provided.

The dividing edge 17 extends in accordance with FIG. 1 from the end face 20 up to a step 22 of the housing 2 of the static mixer which surrounds the collection space 23. The step 22 connects the inlet region of the housing 2 extending from the inlet end 10 up to an inner surface 21 to the mixing space containing the static mixing elements 3.

When assembled, the tubular element is pushed in a first step into the second hollow space of the outlet element of the housing 2. The mixer elements 3 are then positioned in the housing 2 of the static mixer 1. The intermediate piece 4 is connected in a second step to the inlet region 26 of the housing 2, for example via the holding flange 14 which is designed for engagement into the groove 15 which extends along the inner wall of the inlet region 26. For this purpose, the element 16 is aligned visually to the static mixer so that the static mixer 1 and the intermediate piece 4 are assembled in a precisely matching position to one another. The static mixer 1 and the intermediate piece 4 are then introduced into the coupling element 5. The intermediate piece 4 is equipped with a flange 9 which engages into a groove 13 which is located on the inside of the wall 12. The coupling element 5 is then connected via the bayonet fastening means 6 to the dispensing device or to the dispensing cartridge. This connection is only established when the encoding means 50 engages into a reception means of the dispensing device or of the dispensing cartridge. In this state, the system is prepared for the mixing of the components.

FIG. 2 shows a section through a static mixer in accordance with a second embodiment of the invention which is assembled with a cartridge to form a unit. The intermediate piece 4 is made up of the first connection element 24, the flange 9 and the second connection element 25. A plurality of passages 30, 40 extend through the first connection element 24, the flange 9 and the second connection element 25. Components to be mixed are directed from a dispensing device or from a dispensing cartridge through the passages 30, 40 to a static mixer 1 in which the two components meet and are mixed. There is a plurality of different dispensing devices or dispensing cartridges which serve for the storage and for the transport of the individual components. Furthermore, depending on the desired mixing ratio and the required throughput, different types of static mixers are used. These static mixers can differ by their installations, whereby the flow speed and the flow guidance changes; they can have different outer diameters so that different volume flows can be processed so that a throughput characteristic for the type of the static mixer can be achieved.

The user thus has a variety of combination possibilities available depending on the requirements. However, to be able to combine any desired dispensing devices or dispensing cartridges with any desired mixers, the intermediate piece 4 is used. The passages 30, 40 of the intermediate piece 4 have inlet openings 31, 41 which can engage into a dispensing means of a dispensing device or dispensing cartridge or into which a dispensing means can engage. The second connection element 25 can also be made of two pipe pieces which project away from the inlet side of the flange 9. These pipe pieces are received by corresponding outlet openings of the dispensing means on assembly with a dispensing device or a dispensing cartridge, thus plugged into these outlet openings of the dispensing device or of the dispensing cartridge; therefore representing an embodiment of a plug-in connection. An encoding means 50 can be provided to locate the intermediate piece 4 in the correct position with respect to the dispensing device or the dispensing cartridge, FIG. 2 shows a section through an apparatus for the injection of a fluid filler material in accordance with a second embodiment of the invention. The apparatus is part of a device which includes a static mixer 1, an intermediate piece 4 and a cartridge 51. The static mixer 4 is connected to a cartridge 51 via the intermediate piece 4. This cartridge includes a first storage chamber 52 and a second storage chamber 53. The filling volume of the first storage chamber 52 differs from the filling volume of the second storage chamber 53.

This device is used to mix two components in different mixing ratios, with the mixing ratio in particular being able to amount to 4:1 or 10:1. A dispensing device, not shown, can be used to convey the filler material contained in the first and second storage chambers into the static mixer via the intermediate piece 4. The intermediate piece has a first passage 30 and a second passage 40 for this purpose. The inlet opening 31 of the first passage 30 and the inlet opening 41 of the second passage 40 are arranged in this embodiment at tubular stubs which engage into corresponding first and second discharge passages 54, 55 for the components of the filler material. The first discharge passage 54 is arranged at the first storage chamber 52 and the second discharge passage 55 is arranged subsequent to the second storage chamber 53.

The filler material being discharged from the static mixer 1 moves into the outlet element 45. The outlet element 45 is also made as a cone 46 in this embodiment. The cone 46 contains a second hollow space 48 which is suitable to receive and convey the filler material being discharged from the first hollow space 47. The hollow space 47 is formed by the inner space of the mixer housing 2 and contains at least one static mixer element 3.

A tubular element 60 which serves for the dispensing of the filler material to the destination location is arranged in the second hollow space 48. The tubular element 60 will be described in more detail in the following.

FIG. 3 shows a section through a tubular element in accordance with a first embodiment of the invention. The tubular element 60 is received in the outlet element 45. The outlet element 45 is arranged subsequently to the mixer housing 2 and can form one integral piece with the mixer housing 2. The mixer housing 2 contains a first hollow space 47 which serves as a closed passage for the filler material. The first hollow space 47 merges into the second hollow space 48 which contains the tubular element 60. The tubular element 60 is partly received in the second hollow space 48 and projects beyond the discharge opening 70 of the outlet element 45. The tubular element 60 contains a closed passage 56 which leads from the first or second hollow space 47, 48 to the opening aperture 61 of the passage 56 for the conveying of the filler material.

The tubular element 60 is bendable and is shown with a curvature in FIG. 3. The position of the opening aperture 61 of the tubular element 60 can hereby be changed relative to the static mixer 1. The property that the tubular element 60 is bendable can, on the one hand, be due to the fact that the material of the tubular element 60 itself is bendable.

The tubular element 60 furthermore has a widened portion of the passage 56 in the region of the inlet opening 65. This widened portion serves for the reception of an assembly tool. An assembly tool can engage into the widened portion to position and hold the tubular element in the second hollow space. A blow can be exerted onto the tubular element by means of the assembly tool, whereby the tubular element 60 is held firmly in the hollow space 48. The inner diameter of the second hollow space 48 is smaller than the outer diameter of the tubular element 60 at least in the region adjacent to the discharge opening 70.

When assembled, the tubular element 60 is pushed into the second hollow space 48 from the mixer side. The tubular element is then driven through the second hollow space 48 by one blow or by a series of blows by means of an assembly tool while applying a compressive force, for example, until a large part of the tubular element projects out of the discharge opening 70. The widened portion 57 serves in this respect for centering of the assembly tool and for the transmission of the impact force.

FIG. 4 shows a view of a tubular element 60 in accordance with a second embodiment of the invention which, alternatively or in addition to the tubular element 60 shown in FIG. 3, includes at least one bending element 62. A bending element 62 can, for example, include a plurality of thickened portions 63. Regions with lower wall thicknesses, for example restricted portions 64, are arranged between adjacent thickened portions 63 and can be deformed more easily than the two first and second ends 71, 72 of the tubular element 60 extending from the thickened portions. These first and second ends 71, 72 have a larger wall thickness than the restricted portions 64. A single restricted portion 64 can naturally also be provided. The restricted portion can also include a region with a reduced wall thickness which extends between the first end 71 and the second end 72. The thickened portions 63 can be made as ribs or scales, for example. The thickened portions can also have a wave-shaped section. A thickened portion is defined in this respect as a section in which the wall thickness is larger than in the two directly adjoining sections. The wall thickness in this respect can be larger or also the same size as the wall thickness of the tubular element 60 in the region of the first or second ends 71, 72. It is important that the wall thickness is locally smaller between adjacent thickened portions than the wall thickness of the tubular element from the restricted portion 74 disposed closest to the first end 71 up to the inlet opening 65 or from the restricted portion 73 disposed closest to the second end 72 up to the opening aperture 61. The choice of the number and of the profile of the restricted portions is preferably to be designed such that a curvature of the tubular element 60 results which occurs along a curvature curve of constant or continuously changing radius. It is advantageous if the tubular element has no kink or at most a plurality of small kinks so that the flow of the fluid in the curvature region is deflected as smoothly as possible.

The tubular element 60 also has a widened portion 58 in accordance with this embodiment. The widened portion in this case not only includes the passage 56, which is not visible in this representation, but also the jacket 66 of the tubular element 60.

In accordance with the embodiment of FIG. 4 or in accordance with FIG. 12, the widened portion 58 can already be attached to the tubular element before it is installed into the outlet element 45; however, it can also result from the engagement of the assembly tool.

A widened portion in accordance with the embodiment of FIG. 4 and of FIG. 12 has the further advantage that the filler material backs up less in the region of the inlet opening 65. The transition from the second hollow space 48 with a diameter corresponding essentially to the diameter of the static mixer to the passage 56 whose diameter amounts to a maximum of around one millimeter thus takes place gradually since the widened portion 57 results in a narrowing of the passage cross-section for the filler material. The reduction in the passage cross-section for the filler material, viewed in the flow direction, results in a small pressure loss and consequently in a reduction in the pressure drop from the storage containers of the cartridge up to the opening aperture 61 of the tubular element.

FIG. 5 shows a section through the tubular element 60 of FIG. 3 along the plane A-A. It shows the jacket 66 of the tubular element as well as the passage 56 for the filler material which extends through the tubular element 60 in the longitudinal direction. In accordance with a further preferred embodiment, the tubular element 60 includes a jacket 66 of metal. A tubular element 60 of metal is simple to manufacture and can be bent manually into any desired position and is thus bendable. The user can thus adapt the position of the opening aperture 61 of the tubular element 60 in a simple manner to the desired application location of the filler material.

FIG. 6 shows a section in accordance with a third embodiment of the tubular element 60 in accordance with the invention. The jacket 66 of metal or of a bendable plastic can be covered by a plastic layer 67.

The tubular element 60 can also be made of a plastic which contains a bending element 62 in accordance with one of the preceding variants.

FIG. 7 shows a section of a fourth embodiment of the tubular element 60, with a core element 68 which is arranged inside the tubular element 60 being able to be provided for the stabilization of the tubular element 60. The core element 68 can be made for example as a metal pin, in wire form. The core element is used for the setting of the position of the opening aperture 61 of the tubular element 60.

The jacket 66 of the tubular element 60 can be made from any desired deformable material. In this case the deformation of the material of the jacket 66 can be in the elastic region or in the plastic region. The tubular element 60 must be suitable to conduct the filler material, which is discharged from the first hollow space 47 of the static mixer 1, enters into the second hollow space 48 and moves from it into the passage 56 of the tubular element 60 to the desired application location. The position of the opening aperture 61 is fixed by the core element 68. The core element 68 extends in accordance with FIG. 7 freely in the interior of the tubular element 60, thus it is arranged in the passage 56. If the tubular element is bent, this has the consequence that the core element 68 is likewise bent. The core element is plastically deformed in the bending process. The jacket 66 of the tubular element can likewise be plastically deformed, but can also be elastically deformed. However, the bending is maintained by the plastically deformed core element 68. The elastic restoration forces which act on the jacket 66 of the tubular element are not sufficient to reverse the plastic deformation of the core element 68. The tubular element therefore remains in the position which has been preset by the bending process as long as a further bending process is not initiated.

FIG. 8 shows a section of a fifth embodiment of the tubular element 60 which, unlike FIG. 7, is connected to the core element 68 by means of a connection element 69. A plurality of connection elements 69 can naturally also be arranged at different locations in the tubular element 60. The connection element 69 is thus directly located in the passage 56 of the flow of the filler material. The filler material can additionally be stirred by a suitable arrangement of the connection element 69 or of a plurality of connection elements.

FIG. 9 shows a section of a sixth embodiment of a tubular element 60 in accordance with the invention which, shows, alternatively to the embodiments shown in FIG. 7 or FIG. 8, a core element 68 which is at least partly enclosed by the jacket 66 of the tubular element 60. In the present representation, the jacket 66 surrounds the core element 68 completely. This variant has the particular advantage that, on the selection of the material of the core material 68, no consideration has to be taken of whether the material of the core element 68 is compatible with the filler material since the core element 68 is not in contact with the filler material. It is mostly avoided in this case that the core element 68 can produce an additional flow resistance in the tubular element 60. The flow path for the filler material through the passage 56 is kept largely free in accordance with this embodiment.

The core element 68 can in each case be made in wire form in the embodiments shown in FIGS. 6, 7 and 8. The core element 68 can in particular contain a metal. The core material 68 can also be jacketed by a material or coated by a material which is compatible with the filler material or has other advantages specific to the application such as good haptic or optical properties or better compatibility, in particular on use in the dental area.

The core element 68 can alternatively to this also be completely received in the wall of the jacket of the tubular element, which is not shown in the drawing. A plurality of core elements can also be provided which form a reinforcing structure. The core elements can be placed individually in the jacket or can be connected to one another. The core elements can also be made as a grid-shaped structure, as a fiber, felt, fabric or knitwear which is surrounded or enclosed at least partly by the material of the jacket of the tubular element.

FIG. 10 shows a static mixer 101 which is attached to a cartridge 108 as well as an attachment according to the prior art. The cartridge 108 includes a first storage container 111 and a second storage container 112. The first storage container 111 contains a first component of a fluid filler material and the second storage container 112 contains a second component of the fluid filler material. The first component can be conveyed through the first passage 109 into the mixer housing 102; the second component can be conveyed through the second passage 110 into the mixer housing. The first passage 109 and the second passage 110 are guided in tubular stubs (116, 117) which are part of the cartridge 108.

An inlet element 118 which is made in one piece with the mixer housing 102 is attached to the tubular stub. The inlet element 118 has two projections (106, 107) which are in engagement with a fastening means 119 to hold the static mixer in firm connection with the cartridge 108.

After the discharge from the passages 109 and 110, the two components combine to a single flow forming the fluid filler material. This fluid filler material is conveyed through the passages 109 and 110 by application of a contact pressure onto the storage container 111 and 112 and is guided in the interior of the mixer housing by the static mixer elements 103 and subsequently moves from the static mixer to the attachment 113. The attachment 113 is placed onto the discharge end of the static mixer in the present representation and therefore has a diameter matching to the discharge opening 114 of the static mixer 101, which is shown in section in FIG. 11.

FIG. 11 shows a section through the attachment 113 of FIG. 10. The attachment 113 is a conical plastic tube which is approximately 20 mm long. At the tip of the cone, its outer diameter amounts to approximately 3 mm and its inner diameter amounts to approximately 1.5 mm. The outer diameter at the coupling point to the discharge opening 114 of the static mixer corresponds at least to the inner diameter of the discharge opening 114. A ring-shaped abutment 115 is furthermore shown in FIG. 10 whose diameter corresponds to the outer diameter of the discharge opening 114.

FIG. 12 shows a section through a tubular element in accordance with a seventh embodiment of the invention. The tubular element 60 is received in the outlet element 45. The outlet element 45 is arranged subsequent to the mixer housing 2 and is formed in one piece with the mixer housing 2. The mixer housing 2 contains a first hollow space 47 which serves as a closed passage for the filler material. The first hollow space 47 merges into the second hollow space 48 which contains the tubular element 60. The tubular element 60 is partly received in the second hollow space 48 and projects beyond the discharge opening 70 of the outlet element 45. The tubular element 60 contains a closed passage 56 which leads from the first or second hollow space (47, 48) to the opening aperture 61 of the passage 56 for the conveying of the filler material.

The tubular element 60 is bendable and is shown with a curvature in FIG. 12. The position of the opening aperture 61 of the tubular element 60 can hereby be changed relative to the static mixer 1. The tubular element 60 in particular contains a bending element 62 which is made such that the bending element has a bellows structure 75. The bellows structure 75 includes, seen in an axial section, a ring fold 76 of a zigzag profile which forms the bellows structure in this embodiment. This ring fold is made up of a first side 77 and of a second side 78 and of a circumferentially extending edge 79 which is enclosed by the two sides 77, 78. The edge 79 shall from now on be called an uphill edge. As a rule, a plurality of these folds 76 are arranged in rows next to one another and thereby form the bellows structure 75. Adjacent folds 76, 86 are connected via an edge 80 which connects the right hand side end 81 of the first fold arranged at the left hand side 76 to the left hand side end 82 of the second fold 86 arranged at the right hand side. The terms left hand side and right hand side in this respect relate to the representation in FIG. 12, but should only serve for explanation and should in no way be interpreted as to be restricted in any way to the position in the drawing. This edge 80 shall be called a downhill edge in the further text. A first uphill edge 79 thus follows a first downhill edge 80 in the region of the bending element and a second downhill edge 83 then adjoins the first downhill edge 80. The first fold 76 extends between the first downhill edge 80 and the second downhill edge 83. A second fold 86, which is bounded by the second downhill edge 83 and by a third downhill edge 85, follows the first fold 76. The second uphill edge 84 of the second fold 86 rises between the second downhill edge 83 and the third downhill edge 85. The jacket of the tubular element 60 is kinked along each of the edges 79, 80,

83, 84, 85. The wall thickness of the edges 79, 80, 83, 84, 85 in this respect corresponds substantially to the wall thickness of the sides 77, 78. If the bending element is already produced during the manufacture of the tubular element, the wall thickness of the bellows structure can be set as desired. The wall thickness can in particular be selected such that, in the folded state, the tubular element extends along a straight longitudinal axis and remains stable in the straight position. This type of manufacture is in particular suitable for tubular elements which are manufactured in the injection molding process in a single workstep.

The bellows structure 75 can alternatively to this also be applied subsequently after completion of the bending element 62 by plastic deformation of the tubular element 60. In this case, the tubular element will be manufactured by extrusion or by a corresponding continuous manufacturing process for a semifinished part from a metallic material which is subsequently cut to the desired length and the bellows structure can be applied subsequently by means of a shaping process which can include a stamping process or a pressing process. However, for tubular elements made of plastic the bellows structure can, alternatively thereto, be applied directly subsequently to the extrusion of the tubular element 60.

The bellows structure 75 has the effect that the tubular element 60 has a straight longitudinal axis 87 as long as no forces for generating a curvature are applied to the tubular element. However, if bending forces are applied to the bending element which are aligned normally to the longitudinal axis or at least have force components in the normal direction to the longitudinal axis, the straight longitudinal axis will be curved in the region of the bending element. The bending element can be plastically deformed in the edges of the folds by the effect of the bending forces so that the bend of the bending element is irreversible and the bending element remains in the curved position. A stability against kinking is additionally ensured by the peripheral bellows structure. This means that the inner cross-sectional surface of the tubular element 60 in the region of the bending element 62 does not deviate substantially from the inner cross-sectional surface of the first and second sections 88, 89 which adjoin the bending element.

In addition to the preceding statements on a bending element 62 which includes a bellows structure 75, provision can also be made that the bellows structure is held under a prestress. In particular when the angle included between two adjacent sides 77, 78 becomes small, or even tends toward zero, a pretension can be applied during the manufacture of the tubular element which holds the folds 76, 86 in a tightly contacting position with respect to one another. This means that the spacings between adjacent folds are so small that the folds are supported on one another. This is shown in FIG. 12 for the two folds which directly adjoin the first section 88.

If a curvature is applied to the bending element and if this curvature of the bending element is maintained as long as the dispensing of the filler material takes place, the pretension will be overcome by application of a tensile force. The angle between adjacent sides 77, 78 include is enlarged by the application of a tensile force. The adjacent sides can now no longer support one another and can no longer impede a curvature. A force is then applied to set the desired curvature. The material can be locally plastically deformed at least in one part of the edges 79, 80, 83, 84, 85 by this force so that the curvature of the bending element is maintained once it is applied. The curvature should in particular not change at least for the duration of the dispensing of the filler material, that is the curvature radius and the angle the two first and second sections 88, 89 of the tubular element extending from the bending element include with one another.

The tubular element 60 furthermore has a widened portion 57 of the passage 56 in the region of the inlet opening 65. This widened portion 57 serves for the fixing of the tubular element 60 in the outlet element 45. The tubular element 60 is held fixedly in the hollow space 48 and can in particular not be pushed out of the second hollow space 48 by the pressure of the filler material. The inner diameter of the second hollow space 48 can be smaller than the outer diameter of the tubular element 60, at least in the region adjacent to the discharge opening 78, so that a press fit results.

On assembly, the tubular element 60 is pushed into the second hollow space 48 from the mixer side. The tubular element is then driven through the second hollow space 48 by means of an assembly tool by applying a compressive force, for instance one blow or by a series of blows, until a large part of the tubular element projects out of the discharge opening 70. The widened portion 57 can in this respect serve for centering the assembly tool and for transmitting the impact force.

Alternatively to this, the tubular element 60 can, in accordance with one of the preceding embodiments, also be placed into the tool for the outlet element 45 or the mixer housing 2. The tubular element 60 is overmolded in this case, thus surrounded by a plastic melt during the injection molding process which is subsequently cooled. In accordance with this variant, the tubular element 60 is thus inserted in a single workstep when the mixer housing is manufactured. It can also be ensured by this method that the cross-sectional surface of the tubular element 60 at the inlet opening is the same as the cross-sectional surface of the second hollow space 48 at this point.

A further variant is shown in FIG. 13. The tubular element 60 is placed into the tool 90 for the mixer housing 2 without a widened portion 57, which is shown in FIG. 13. The inlet opening 65 of the tubular element 60 is engaged by a tool mandrel 91 which is movable. If the tool 90 or the tool mandrel 91 are moved such that the shape of the mixer housing to be manufactured is obtained, the tool mandrel is introduced into the inlet opening 65 of the tubular element. The inlet opening of the tubular element is stretched during this movement of the tool mandrel or of the tool, that is the material of the tubular element is subjected to a plastic deformation. This variant has the advantage that a preceding or subsequent workstep of the widening can be omitted since the widening can already take place during the manufacture of the mixer housing and of the outlet element.

Alternatively to this, it is possible to fasten and hold the tubular element 60 in accordance with one of the preceding embodiments in the second hollow space by means of a snap connection or a holding connection or by means of an adhesive bonding connection.

Furthermore, the tubular element 60 in accordance with one of the preceding embodiments can be arranged rotatably relative to the static mixer, unless it were fastened by an adhesive bonding connection.

The invention claimed is:

1. An apparatus for the injection of a fluid filler material including
    a static mixer having a housing which includes a first hollow space;
    at least one mixing element for mixing the fluid filler material being arranged in the first hollow space,
    said housing having an outlet element having a second hollow space being connected to the first hollow space such that the fluid filler material can be conducted from the first hollow space into the second hollow space;

a tubular element held in the second hollow space and characterized in that said housing is configured as a fastening element for said tubular element, said tubular element being spaced longitudinally from said static mixing element and having an opening aperture at one end for dispensing the fluid filler material therefrom.

2. An apparatus in accordance with claim 1, wherein the tubular element has an outer diameter of a maximum of 3 mm.

3. An apparatus in accordance with claim 1 wherein the tubular element has a length of a maximum of 100 mm.

4. An apparatus in accordance with claim 1 wherein the outlet element includes a cone.

5. An apparatus in accordance with claim 1 wherein the second hollow space is made conically at least section-wise.

6. An apparatus in accordance with claim 1 wherein the second hollow space has an inner diameter which is smaller than the outer diameter of the tubular element.

7. An apparatus in accordance with claim 1 wherein the tubular element is one of bendable and rotatable with respect to the static mixer.

8. An apparatus in accordance with claim 7, wherein the tubular element includes at least one bending element.

9. An apparatus in accordance with claim 1 wherein the tubular element includes a jacket of metal.

10. An apparatus in accordance with claim 9, wherein the jacket of metal is covered by a plastic layer.

11. An apparatus in accordance with claim 1 wherein the tubular element includes a jacket of plastic.

12. An apparatus in accordance with claim 1 wherein the tubular element includes a core element which is arranged within the tubular element.

13. An apparatus in accordance with claim 12, wherein the core element is connected to the tubular element by means of a connection element.

14. An apparatus in accordance with claim 12 wherein the core element is surrounded at least partly by the tubular element.

15. An apparatus in accordance with claim 12 wherein the core element is made in wire form.

16. An apparatus in accordance with claim 12 wherein the core element contains a metal.

17. A dispensing device for a fluid filler material comprising a housing defining a first hollow space and a second hollow space;

a static mixing element disposed in said first hollow space of said housing for mixing a fluid filler material flowing therethrough and dispensing the fluid filler material into said second hollow space;

a tubular element secured to said housing in communication with said second hollow space and spaced longitudinally from said static mixing element, said tubular element projecting from said housing and having an opening aperture at one end for dispensing the fluid filler material therefrom; and a coupling element connected to said housing for fastening said housing to a source of the fluid filler material.

18. A dispensing device as set forth in claim 17 wherein at least said one end of said tubular element is bendable relative to said housing.

19. A dispensing device for a fluid filler material comprising a longitudinally elongated housing defining a first hollow space;

a static mixing element disposed in said first hollow space of said housing for mixing a fluid filler material flowing therethrough and dispensing the fluid filler material therefrom;

a tubular element secured to and within said housing and spaced longitudinally from said static mixing element to define a second hollow space therebetween for the fluid filler material dispensed from said static mixing element, said tubular element projecting from said housing and having an opening aperture at one end spaced from said housing for dispensing the fluid filler material therefrom; and a coupling element connected to said housing for fastening said housing to a source of the fluid filler material.

20. A dispensing device as set forth in claim 19 wherein at least said one end of said tubular element is bendable relative to said housing.

* * * * *